United States Patent
Sakaguchi et al.

(10) Patent No.: US 11,085,987 B2
(45) Date of Patent: Aug. 10, 2021

(54) MAGNETIC RESONANCE IMAGING DEVICE, NYQUIST GHOST CORRECTION METHOD, AND NYQUIST GHOST CORRECTION PROGRAM

(71) Applicant: Hitachi, Ltd., Tokyo (JP)

(72) Inventors: Naoya Sakaguchi, Tokyo (JP); Syouichi Miyawaki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 16/646,254

(22) PCT Filed: Nov. 22, 2018

(86) PCT No.: PCT/JP2018/043202
§ 371 (c)(1),
(2) Date: Mar. 11, 2020

(87) PCT Pub. No.: WO2019/181066
PCT Pub. Date: Sep. 26, 2019

(65) Prior Publication Data
US 2020/0284867 A1 Sep. 10, 2020

(30) Foreign Application Priority Data
Mar. 20, 2018 (JP) .............................. JP2018-053230

(51) Int. Cl.
*G01R 33/565* (2006.01)
*A61B 5/055* (2006.01)
(Continued)

(52) U.S. Cl.
CPC ........ *G01R 33/56554* (2013.01); *A61B 5/055* (2013.01); *G01R 33/4824* (2013.01);
(Continued)

(58) Field of Classification Search
CPC ............ G01R 33/4824; G01R 33/5608; G01R 33/5616; G01R 33/56341; G01R 33/56554; A61B 5/055
See application file for complete search history.

(56) References Cited

U.S. PATENT DOCUMENTS

2007/0055137 A1* 3/2007 Feiweier .......... G01R 33/56554
600/410
2015/0061668 A1 3/2015 Dannels
(Continued)

FOREIGN PATENT DOCUMENTS

| JP | 2009-273530 A | 11/2009 |
| JP | 2015-047507 A | 3/2015 |
| JP | 2015-160141 A | 9/2015 |

OTHER PUBLICATIONS

Nan-kuei Chen et al., Removal of EPI Nyquist Ghost Artifacts with Two-Dimensional Phase Correction, Magnetic Resonance in Medicine, vol. 51, pp. 1247-1253, 2004.
(Continued)

*Primary Examiner* — Gregory H Curran
(74) *Attorney, Agent, or Firm* — Baker Botts L.L.P.

(57) ABSTRACT

The present invention is directed to enabling high-accuracy Nyquist ghost correction without using a reference image. After at least one of a plurality of images for use in diagnosis is used to perform low-order phase correction without causing aliasing of an image, a 2D phase map including remaining high-order phase errors and phase errors in a phase encode direction is calculated. The low-order phase correction is performed on a pair of pieces of data for image obtained by inverting a readout gradient magnetic field as image data for use in 2D phase map calculation, and positive-polarity/negative-polarity errors of the readout gradient magnetic field are calculated with odd lines and even lines of the pair of pieces of data for image rearranged. In the
(Continued)

case of DWI imaging, an image with b-value=0 can be used for 2D phase map calculation.

15 Claims, 15 Drawing Sheets

(51) Int. Cl.
  *G01R 33/48* (2006.01)
  *G01R 33/56* (2006.01)
  *G01R 33/561* (2006.01)
  *G01R 33/563* (2006.01)
(52) U.S. Cl.
  CPC ..... *G01R 33/5608* (2013.01); *G01R 33/5616* (2013.01); *G01R 33/56341* (2013.01)

(56) References Cited

U.S. PATENT DOCUMENTS

| | | |
|---|---|---|
| 2015/0241537 A1 | 8/2015 | Dannels |
| 2016/0041248 A1* | 2/2016 | Chen ................ G01R 33/5616 324/309 |
| 2017/0276755 A1 | 9/2017 | Hoge et al. |
| 2019/0369192 A1* | 12/2019 | McKay ............ G01R 33/56554 |

OTHER PUBLICATIONS

Victor B. Xie et al., Robust EPI Nyquist Ghost Removal by Incorporating Phase Error Correction with Sensitivity Encoding (PEC-SENSE), Magnetic Resonance in Medicine, vol. 79, pp. 943-951, Jun. 7, 2017.

Z. Xiao et al., Efficient DTI Artifact Correction via Spatial and Temporal Encoding, Proc. Intl. Soc. Mag. Reson. Med., vol. 18, p. 3998, 2010.

Yuval Zur, Two-Dimensional Phase Correction Method for Single and Multi-Shot Echo Planar Imaging, Magnetic Resonance in Medicine, vol. 66, pp. 1616-1626, 2011.

International Search Report, dated Feb. 19, 2019, which issued during the prosecution of International Application No. PCT/JP2018/043202, which corresponds to the present application.

International Preliminary Report on Patentability including Written Opinion of the International Searching Authority, dated Sep. 22, 2020, for International Application No. PCT/JP2018/043202.

* cited by examiner

MAGNETIC RESONANCE IMAGING DEVICE, NYQUIST GHOST CORRECTION METHOD, AND NYQUIST GHOST CORRECTION PROGRAM

TECHNICAL FIELD

The present invention relates to a magnetic resonance imaging device (hereinafter referred to as an "MRI device") and, more particularly, to a method for correcting Nyquist ghosts in MRI using an echo planar imaging (EPI) method with a high degree of accuracy.

BACKGROUND ART

An EPI sequence is a sequence of collecting a great number of echo signals while reversing the polarity of a readout gradient magnetic field at highspeed after one excitation and is able to acquire data required for reconstruction of one image in a short time, and is, therefore, widely adopted for imaging of, for example, a diffusion weighted image (DWI), which requires acquisition of a great number of images. In the EPI sequence, in reversing the gradient magnetic field at high speed, due to the influence of, for example, errors in hardware control or eddy current, an error in phase occurs between an odd-numbered echo (odd echo) and an even-numbered echo (even echo) out of echoes which are collected at one time. Thus, an error occurs between an even line and an odd line in k-space, and, if such an image is reconstructed, a ghost artifact occurs at a position deviating by half of a field of view (FOV) in the phase encode direction of an image. This artifact is called a Nyquist ghost or an N/2 artifact, and becomes a hindrance to accurate diagnosis when overlapping a test subject image.

As a method for reducing this artifact, there is a technique to correct an error between an odd echo and an even echo. For example, there is a method of cancelling the error by, when the number of times of addition is two or more, reversing the applied polarity of the readout gradient magnetic field between the odd-number-th imaging and the even-number-th imaging and performing complex addition of the acquired signals on k-space or an image.

On the other hand, DWI imaging is a method of performing imaging with use of a deviation in phase occurring due to diffusion during application of a high-strength gradient magnetic field called motion proving gradient (MPG) pulses, and is, therefore, likely to be affected by a phase change caused by other factors, so that, if complex addition is applied to DWI imaging, image deterioration such as signal loss may be caused. To avoid this, a DWI image is often subjected to addition of an absolute value image, and, therefore, a sufficient effect of reducing Nyquist ghosts cannot be attained.

As another method for reducing Nyquist ghosts, there is a technique which, at the time of preliminary imaging (pre-scan), in addition to adjusting, for example, an irradiation frequency and a receiving gain, activates an SE-EPI sequence, without application of a phase encode gradient magnetic field, acquires an amount of error for every echo signal from data obtained by pre-scan, and then corrects data obtained by main imaging (imaging for acquiring a diagnostic image), which is performed after pre-scan (Patent Literature 1). A deviation of the echo center in k-space caused by a phase error between the odd echo and the even echo appears as a primary gradient at a phase profile in the readout direction in xky-space data obtained by performing Fourier transform of k-space data in the x-direction. By correcting an error of the echo signal acquired by main imaging with use of a phase gradient acquired by preliminary imaging, an error between the odd echo and the even echo can be reduced. While most of the Nyquist ghosts are reduced by the phase correction in this method (hereinafter referred to as "xky correction"), a high-order error in the readout direction or an error in the phase encode direction is unable to be corrected, and, therefore, ghosts may remain in some cases.

As a technique to reduce such remaining Nyquist ghosts, a phase correction method using a two-dimensional phase map has been proposed (Patent Literature 2). This method calculates a correction map with use of an odd reference image obtained from odd lines of reference data obtained by preliminary imaging (pre-scan) and an even reference image obtained from even lines thereof and corrects a diagnostic image with use of the calculated correction map. According to this method, since not only an error between even and odd echoes but also an error in the phase encode direction is concurrently corrected, an appropriate Nyquist ghost reduction effect can be attained even in DWI images.

CITATION LIST

Patent Literature

Patent Literature 1: JP-A-2009-273530
Patent Literature 2: JP-A-2015-47507

SUMMARY OF INVENTION

Technical Problem

However, even in the correction method described in Patent Literature 2, to calculate a phase map from data which is in a state in which aliasing does not occur in an image, it is necessary to acquire a reference image (reference data) with the FOV whose size has been doubled in the phase encode direction, so that there is a disadvantage of involving prolongation of imaging time. DWI is an imaging where a diffusion motion of water molecules is enhanced by MPG pulses, and is, therefore, likely to be affected by a body motion such as breathing or heartbeat, so that there is a high possibility of, for example, an image to be acquired deteriorating as an imaging time becomes longer. Moreover, in functional imaging which acquires time-series images (f-MRI), for example, as a period between the time of acquisition of a reference image used for calculating a phase map and the time of imaging becomes longer, the reliability of correction using a phase map becomes lower due to, for example, a body motion occurring during that period.

An issue of the present invention is to provide a technique to acquire two-dimensional phase correction data (2D phase map), for correcting Nyquist ghosts with a high degree of accuracy, with use of data obtained by imaging for acquiring an image of a test object (main imaging) without acquiring a reference image.

Solution to Problem

To solve the above-mentioned issue, the present invention calculates a 2D phase map with use of data for image obtained by a series of imaging operations for obtaining an image of a test object. The 2D phase map is calculated after reducing aliasing of an image by low-order phase correction while maintaining the same FOV as an FOV for imaging.

More specifically, an MRI device according to the present invention includes a measurement unit that acquires a plurality of pieces of data for image with use of an EPI method, a phase map calculation unit that calculates a phase map using at least one of the plurality of data for image measured by the measurement unit, and a correction unit that corrects a Nyquist ghost included in the data for image with use of the phase map calculated by the phase map calculation unit. The phase map calculation unit performs low-order phase correction with use of a pair of k-space data different in only polarity of readout gradient magnetic field of the data for image used for phase map calculation, and calculates a 2D phase map in which a remaining two-dimensional phase error is set as a correction amount, and wherein, after performing low-order phase correction on data for image targeted for correction, the correction unit performs two-dimensional phase correction thereon with use of the 2D phase map.

Furthermore, each of a plurality of data for image which the measurement unit acquires is data from which an image of a test subject is able to be reconstructed, and, in the present specification, is also referred to as data for image of main imaging as distinguished from data for image of preliminary imaging.

Advantageous Effects of Invention

According to the present invention, since data for image of main imaging is used for phase map calculation, it is possible to eliminate the necessity of preliminary imaging for acquiring reference data. With this, in DWI imaging, which is required to be high-speed imaging, it is possible to obtain a diffusion image with any Nyquist ghosts reduced without involving prolongation of an imaging time, and, moreover, in continuous imaging such as f-MRI, it is possible to shorten a time from phase map acquisition to phase correction and thus reduce an influence of, for example, a body motion. Additionally, according to the present invention, since a 2D phase map is calculated after reducing aliasing of an image by low-order phase correction while maintaining the same FOV as an FOV for imaging, it becomes possible to perform high-accuracy two-dimensional phase correction.

DESCRIPTION OF EMBODIMENTS

<Embodiment of MRI Device>

First, an overall configuration of an MRI device is described with reference to FIG. 1 and FIG. 2.

Figure 1:
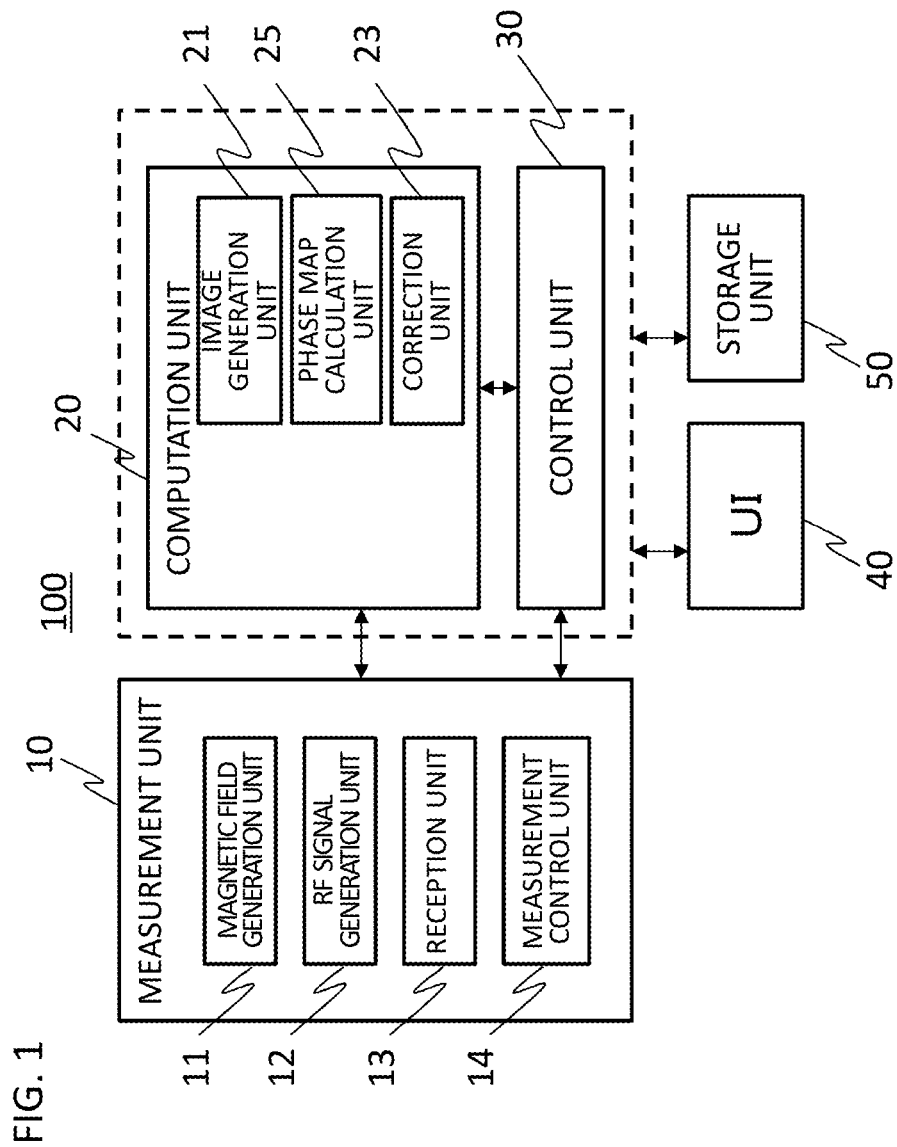
FIG. 1 is a block diagram illustrating an outline of an MRI device according to an embodiment of the present invention.
Figure 2:
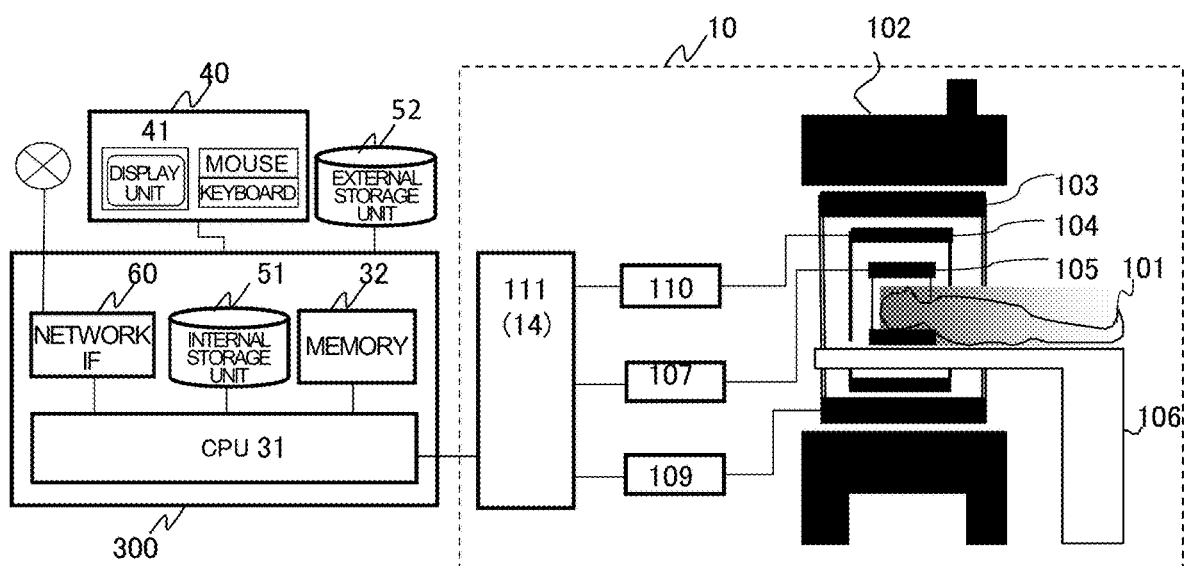
FIG. 2 is a block diagram illustrating a configuration of the MRI device illustrated in FIG. 1.

The MRI device 100 includes, as illustrated in FIG. 1, a measurement unit 10, which collects nuclear magnetic resonance (NMR) signals from a test subject and thus acquires data used to generate an image of the test subject, a computation unit 20, which performs computations, such as correction and image reconstruction, on the data acquired by the measurement unit 10, a control unit 30, which controls operations of the measurement unit 10 and the computation unit 20, a user interface (UI) device 40, which includes, for example, an input device to which the user inputs conditions and numerical values required for operations of the computation unit 20 and the control unit 30 and a display which displays, for example, an image acquired by imaging, and a storage unit 50.

The measurement unit 10 includes a magnetic field generation unit 11, which generates a static magnetic field and a gradient magnetic field, an RF signal generation unit 12, which generates a high-frequency signal for exciting nuclear spins of atomic nuclei of tissues constituting a test subject, a reception unit 13, which receives a nuclear magnetic resonance signal which a test subject generates, and a measurement control unit 14, which controls measurement. Specifically, as illustrated in FIG. 2, the measurement unit 10 includes a static magnetic field generation magnet 102, a gradient magnetic field coil 103, and a gradient magnetic field power source 109, which serve as the magnetic field generation unit 11, an RF transmission coil 104 and an RF transmission unit 110, which serve as the RF signal generation unit 12, an RF reception coil 105 and a signal processing unit 107, which serve as the RF reception unit, and a sequencer 111, which serves as the measurement control unit 14, and further includes a bed 106 which carries a top board, on which a test subject 101 is placed, into and out of a static magnetic field space formed by the static magnetic field generation magnet 102.

The static magnetic field generation magnet 102 is configured with a static magnetic field generation device of the permanent magnet type, the normal conductivity type, or the superconductivity type, and is of one of the vertical magnetic field type and the horizontal magnetic field type according to the direction of a magnetic field to be generated. When being of the vertical magnetic field type, the static magnetic field generation magnet 102 generates a homogeneous static magnetic field in a direction perpendicular to the body axis of the test subject 101, and, when being of the horizontal magnetic field type, the static magnetic field generation magnet 102 generates a homogeneous static magnetic field in the direction of the body axis of the test subject 101.

The gradient magnetic field coil 103 includes coils respectively wound in directions of three axes X, Y, and Z which configure a real-space coordinate system (a stationary coordinate system) of the MRI device, and each gradient magnetic field coil is connected to the gradient magnetic field power source 109, which drives the gradient magnetic field coil, and is supplied with current from the gradient magnetic field power source 109. Specifically, the gradient magnetic field power sources 109 for the respective gradient magnetic field coils are respectively driven according to instructions from the sequencer 111 and supply currents to the respective gradient magnetic field coils. With this, gradient magnetic fields Gx, Gy, and Gz are generated in the directions of three axes X, Y, and Z, and a combination of these gradient magnetic fields in the directions of three axes forms gradient magnetic fields in optional directions. For example, during imaging for a two-dimensional slice plane, slice gradient magnetic field pulses (Gs) are applied in a direction perpendicular to a slice plane (imaging cross-section) to set a slice plane with respect to the test subject 101, and phase encode gradient magnetic field pulses (Gp) and frequency encode (readout) gradient magnetic field pulses (Gf) are applied in the remaining two directions perpendicular to the set slice plane and perpendicular to each other, so that pieces of positional information in the respective directions are encoded into an NMR signal (also referred to as an "echo signal").

The RF transmission coil 104, which is a coil used to radiate RF pulses to the test subject 101, is connected to the RF transmission unit 110 and is supplied with a high-frequency pulse current. With this, an NMR phenomenon is induced in spins, typically, protons, of atoms constituting a body tissue of the test subject 101. Specifically, the RF transmission unit 110 is driven pursuant to an instruction from the sequencer 111 to amplitude-modulate and amplify high-frequency pulses and then supply the high-frequency pulses to the RF transmission coil 104, which is located in proximity to the test subject 101, so that RF pulses are radiated onto the test subject 101.

The RF reception coil 105, which is a coil used to receive an echo signal emitted by the NMR phenomenon of spins constituting a body tissue of the test subject 101, is connected to the signal processing unit 107, so that the received echo signal is transmitted to the signal processing unit 107.

The signal processing unit 107 performs processing for detecting an echo signal received by the RF reception coil 105. Specifically, pursuant to an instruction from the sequencer 111, the signal processing unit 107 amplifies the received echo signal, divides the amplified echo signal into signals of two orthogonal channels by orthogonal phase detection, performs sampling of each of the signals of two orthogonal channels by predetermined numbers (for example, 128, 256, and 512), and then A/D-converts the obtained sampling signals into respective digital amounts. Accordingly, an echo signal is obtained as time-series digital data (hereinafter referred to as "k-space data") configured with a predetermined number of pieces of sampling data.

The sequencer 111 controls the gradient magnetic field power source 109, the RF transmission unit 110, and the signal processing unit 107 based on control data for a predetermined pulse sequence, repeatedly performs radiation of RF pulses and application of gradient magnetic field pulses to the test subject 101 and detection of echo signals from the test subject 101, and thus controls collection of echo data required for reconstruction of an image with respect to an imaging region of the test subject 101.

In the MRI device according to the present embodiment, the measurement control unit 14 (sequencer 111) performs control that is based on an EPI sequence serving as the predetermined pulse sequence. The EPI sequence is, as mentioned above, a sequence of collecting a plurality of echo signals by performing sampling of echo signals during application of a readout gradient magnetic field for each polarity while reversing the polarity of readout gradient magnetic field after application of RF excitation pulses performed once, and SE-EPI including excitation pulses and reverse pulses as RF pulses is also applied to the present embodiment.

Figure 3:
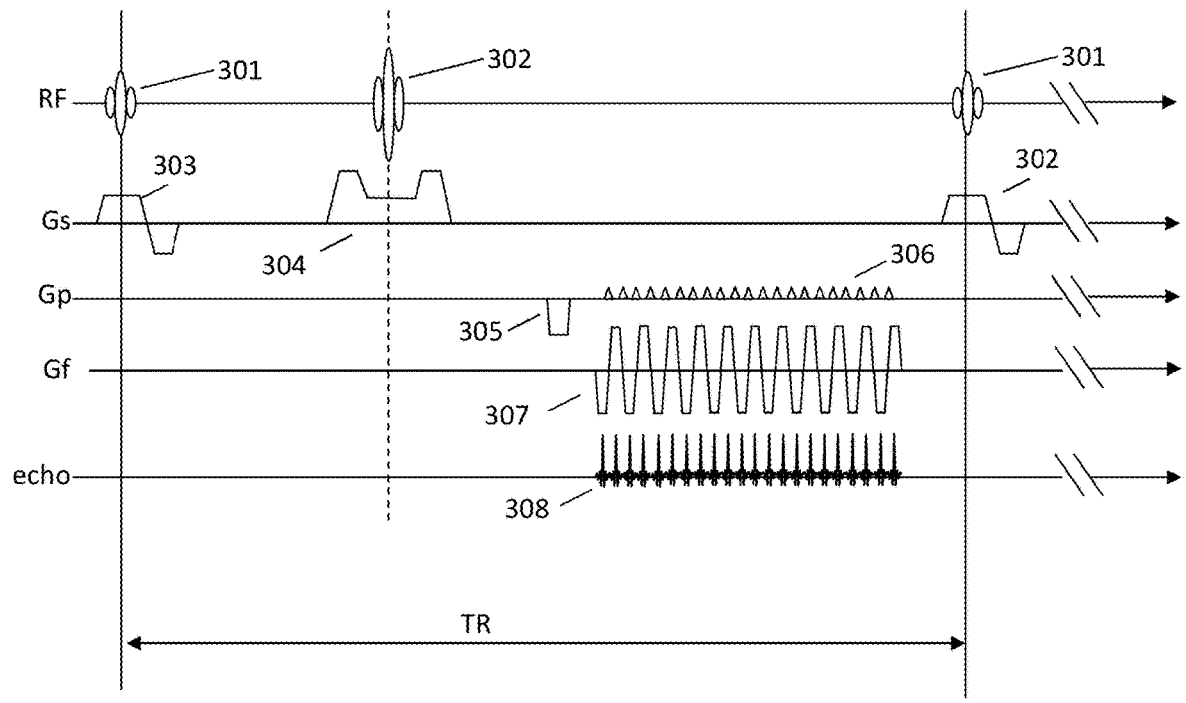
FIG. 3 is a diagram illustrating an example of a pulse sequence which is caused to operate by the MRI device of the present invention.

An example of the SE-EPI sequence is illustrated in FIG. 3. The EPI sequence first applies RF pulses for excitation 301 as well as a slice selection gradient magnetic field 303 and, after that, applies reverse RF pulses 302 as well as a slice selection gradient magnetic field 304, thus exciting a desired slice. Next, the EPI sequence applies a phase encode gradient magnetic field 305 and, after that, continuously applies a blip-like phase encode gradient magnetic field 306 and a readout gradient magnetic field 307 with the polarity thereof repeatedly reversed, thus collecting echo signals 308 during application of the repeatedly-reversing readout gradient magnetic field 307. If a single-shot EPI is employed, the EPI sequence measures all of the echo signals the number of which corresponds to a number of echo signals required for image reconstruction by excitation performed once.

Such a pulse sequence is set to the measurement control unit 14 via, for example, the UI device 40 together with imaging conditions such as an echo time (TE), a repetition time (TR), and a field of view (FOV).

The computation unit 20 performs computations such as image reconstruction or correction of k-space data collected by the measurement unit 10, and causes an image of the test subject 101, which is a processing result of those computations, to be displayed on a display unit 41 of the UI device 40, to be recorded on the storage unit 50, such as an internal storage unit 51 or an external storage unit 52, or to be transferred to an external device via a network interface (IF) 60.

The control unit 30 controls the entire device, for example, the measurement control unit 14, the computation unit 20, and the UI device 40. In the embodiment illustrated in FIG. 2, a computer 300 including a CPU 31 and a memory 32 implements the functions of the computation unit 20 and the control unit 30. Programs for computation and control can be previously stored in a storage device, or can be fetched in from the outside and be uploaded and executed by the CPU. Furthermore, a part of the functions of the computation unit 20 can be implemented by hardware such as an application specific integrated circuit (ASIC) or a field programmable gate array (FPGA).

The MRI device according to the present embodiment is characterized by including, as the functions of the computation unit 20, a correction unit which corrects for Nyquist ghosts in an image obtained by the EPI sequence, and, specifically, includes, as illustrated in FIG. 1, an image generation unit 21 which reconstructs an image by performing Fourier transform on k-space data collected by the measurement unit 10 or generates, for example, a composite image or a calculated image with use of a reconstructed image, a correction unit 23 which performs correction such as phase correction on an image, and a phase map calculation unit 25 which calculates data for correction required for phase correction to be performed by the correction unit 23, here, a 2D phase map. Although not illustrated in FIG. 1, the computation unit 20 may, in some cases, include the function of calculating, for example, various amounts representing the characteristics of a test subject with use of an image generated by the image generation unit.

Next, in light of the above-described configuration of the computation unit 20, an embodiment of an operation of the MRI device, mainly, processing for two-dimensional phase correction, is described.

First Embodiment

The present embodiment performs DWI imaging as imaging for acquiring a plurality of pieces of image data by an EPI method. Moreover, the present embodiment calculates a 2D phase map with use of image data obtained by imaging (b-value=zero) which does not apply MPG pulses in DWI imaging, and performs Nyquist ghost correction for DWI images other than those with b-value=zero with use of the calculated 2D phase map.

First, a procedure of DWI imaging according to the present embodiment is described.

Figure 4:
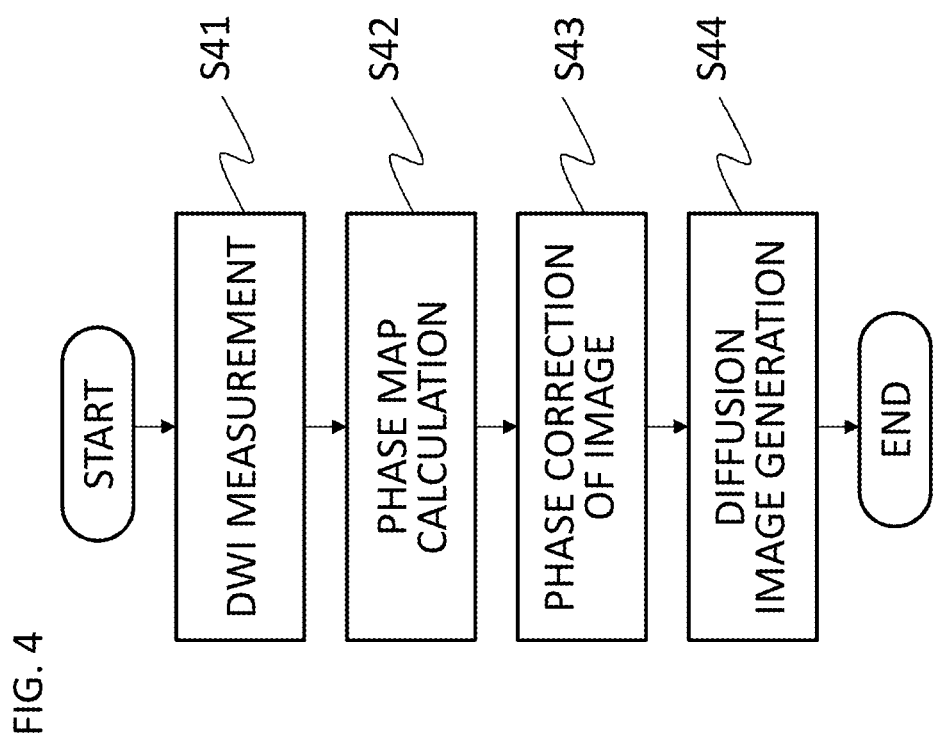
FIG. 4 is a diagram illustrating a procedure of imaging in a first embodiment.

As illustrated in FIG. 4, DWI imaging according to the present embodiment includes a measurement step S41 which collects signals for image generation while making intensities of MPG pulses different from each other in a plurality of directions, a phase map calculation step S42 which uses data for image acquired without application of MPG pulses out of pieces of data for image obtained by measurement, a step S43 which corrects the data for image acquired in step S41 with use of a phase map calculated in step S42, and a step S44 which calculates, for example, a diffusion weighted image (a diffusion trace image) or an apparent diffusion coefficient (ADC) map, in which ADCs are set as pixel values, with use of the corrected data for image. In the following description, for example, a diffusion trace image and an ADC map are collectively referred to as a "diffusion image" or "DWI image". In the conventional DWI imaging, prior to the measurement step S41 for collecting signals for image generation, a pre-scan which collects signals for reference image used for Nyquist ghost correction has been performed. The reference image has been required to be generated using a pulse sequence with the FOV doubled in the phase encode direction, with respect to an image to be acquired. However, in the present embodiment, since a phase map is calculated with use of data for image acquired in the measurement step S41, such a pre-scan is unnecessary and is thus not performed.

Details of each step are described as follows.

[Measurement Step S41]

Figure 5:
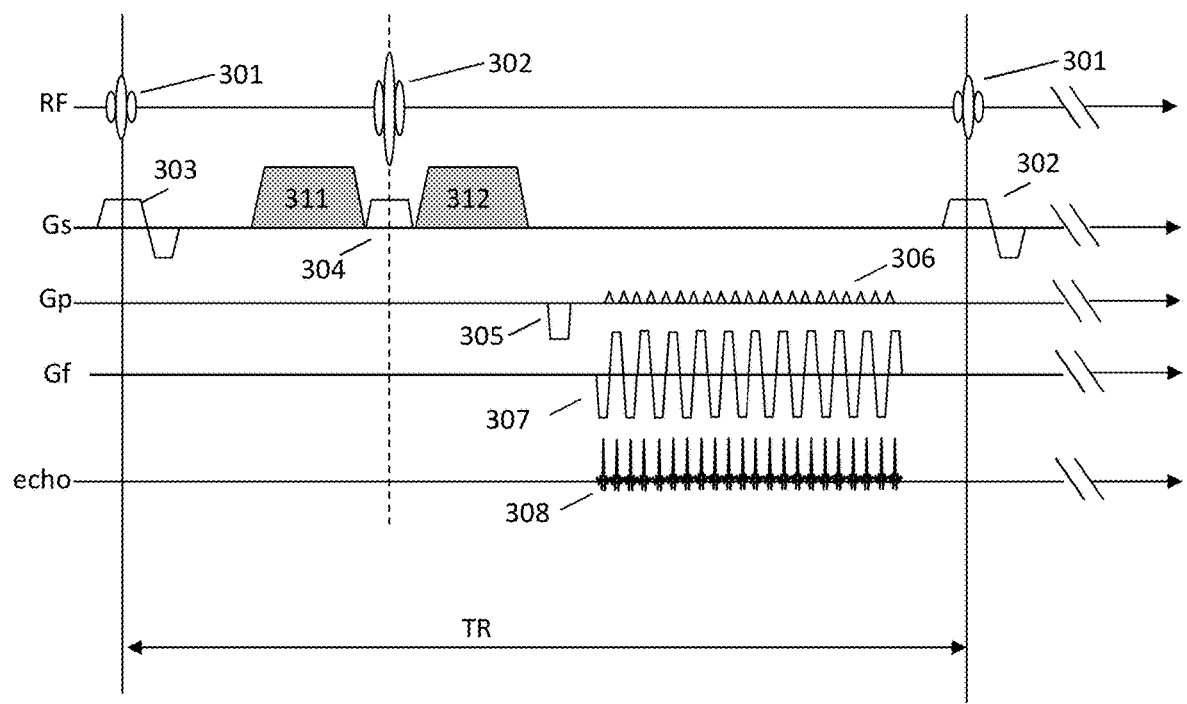
FIG. 5 is a diagram illustrating an example of a DWI pulse sequence which is caused to operate in the first embodiment.

In the measurement step S41, under the control of the measurement control unit 14, the measurement unit 10 performs a DWI sequence that is based on, for example, an SE-EPI sequence such as that illustrated in FIG. 3. FIG. 5 illustrates an example of the DWI sequence. In FIG. 5, the same elements as those illustrated in FIG. 3 are denoted by the respective same reference characters and are omitted from description. As illustrate in FIG. 5, in the DWI sequence, high-intensity MPG pulses 311 and 312 are applied before and after the reverse RF pulses 302, respectively. While FIG. 5 illustrates a case where MPG pulses are applied along the axis of a slice gradient magnetic field Gs, DWI usually performs a plurality of times of imaging while making axes (directions) along which MPG pulses are applied, different from each other. Moreover, DWI repeats imaging while varying intensities (b-values) of MPG pulses with respect to respective directions. Variation of the intensity also includes the case of b-value=0, in other words, a case illustrated in FIG. 3 where MPG pulses are not applied. However, imaging with b-value=0 is common to the respective directions and only needs to be performed once.

Figure 6:
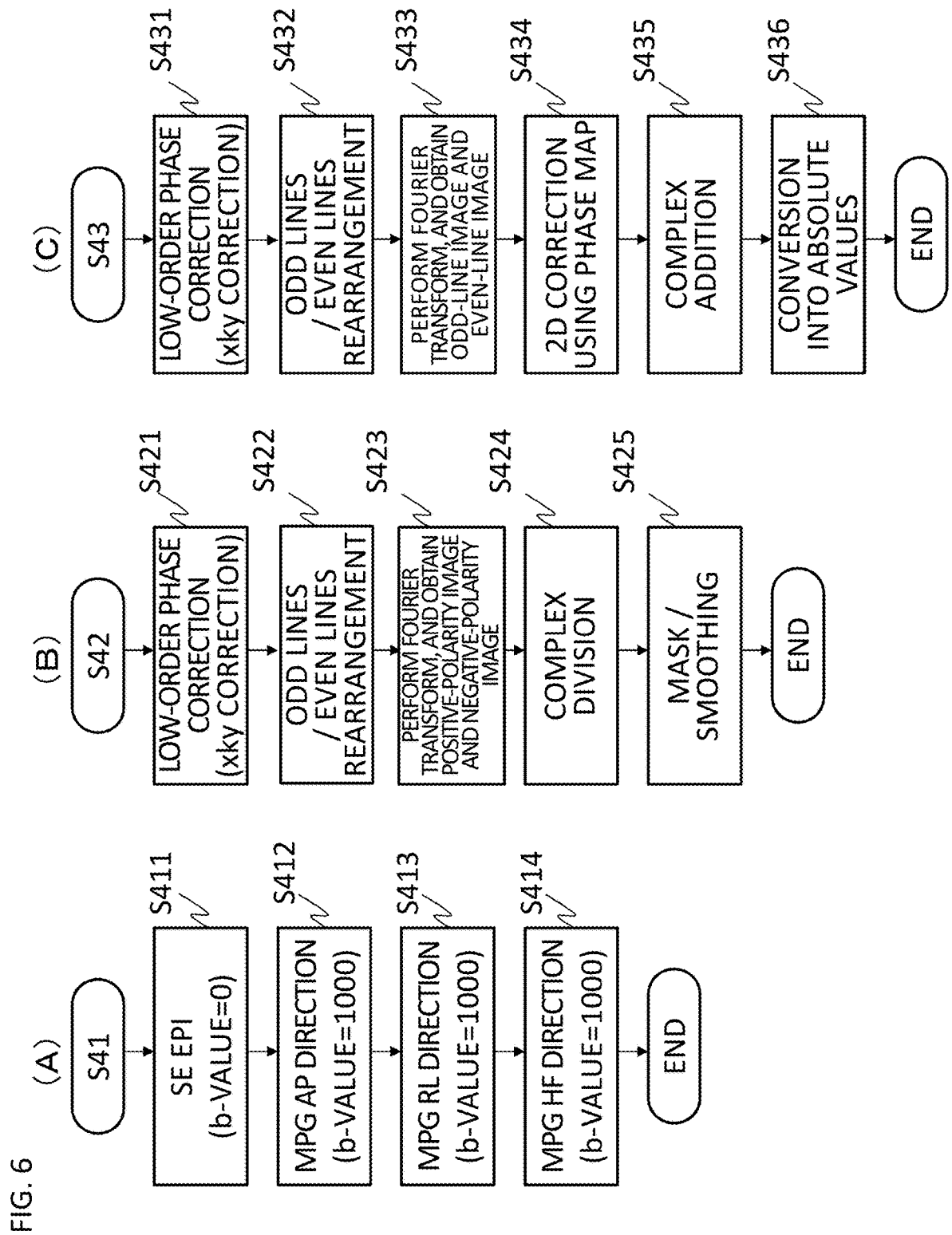
FIG. 6 is a diagram illustrating details of each step illustrated in FIG. 4, in which (A) illustrates a measurement step, (B) illustrates a phase map calculation step, and (C) illustrates a correction step.

FIG. 6(A) illustrates an example of the measurement step S41. In the procedure illustrated in FIG. 6(A), an example in which, in addition to imaging with b-value=0 performed once (S411), a pulse sequence which applies MPG pulses in three directions, i.e., AP-direction (anteroposterior direction), RL-direction (right-left direction), and HF-direction (body-axis direction), is performed is illustrated (S412 to S414). While MPG pulses in the case of b-value=1000 are illustrated as an example, MPG pulses in the case of a b-value other than the above value can also be employed, or imaging can be performed with a plurality of b-values. Moreover, although the number of times of addition in each imaging is optional, imaging with b-value=0 (S411) is performed two times while the application polarity of readout gradient magnetic field is reversed to calculate phase map in the next step. Furthermore, the method of reversing the application polarity can also be implemented by, in addition to a method of reversing a readout gradient magnetic field itself, increasing or decreasing the area of the phase encode gradient magnetic field 305 illustrated in FIG. 3 by one blip 306 or an odd number of blips 306.

[Phase Map Calculation Step S42]

In the phase map calculation step S42, as illustrated in FIG. 6(B), the phase map calculation unit 25 performs low-order phase correction to data obtained before being converted into a real space (S421), and then calculates a phase map (2D phase map) representing remaining phase errors, such as high-order phase errors, with use of data obtained by being converted into a real space (S425). The low-order phase correction is applied to, for example, a pair of pieces of measurement data obtained by imaging with b-value=0 performed in the measurement step S41 (a pair of pieces of measurement data obtained with the application polarity of readout gradient magnetic field reversed) and is performed to k-space (kxky-space) data or xky-space data obtained by Fourier-transforming the k-space data in the readout direction (S421). Then, odd lines and even lines are rearranged to separate between echoes collected by applying a readout gradient magnetic field to the positive electrode and echoes collected by applying a readout gradient magnetic field to the negative electrode (S422). The low-order phase correction can include processing (xky correction) for correcting errors (primary gradient) between odd echoes and even echoes in xky-space, thus enabling improving the accuracy of a phase map which is subsequently calculated.

The phase map calculation unit 25 acquires the phase map by performing complex division on a pair of pieces of real space data subjected to low-order correction, that is, a positive-polarity image and a negative-polarity image (S423 and S424). On this occasion, mask processing, smoothing processing for removing phase information other than that in a test subject region (S425) or the like may be performed.

Figure 7:
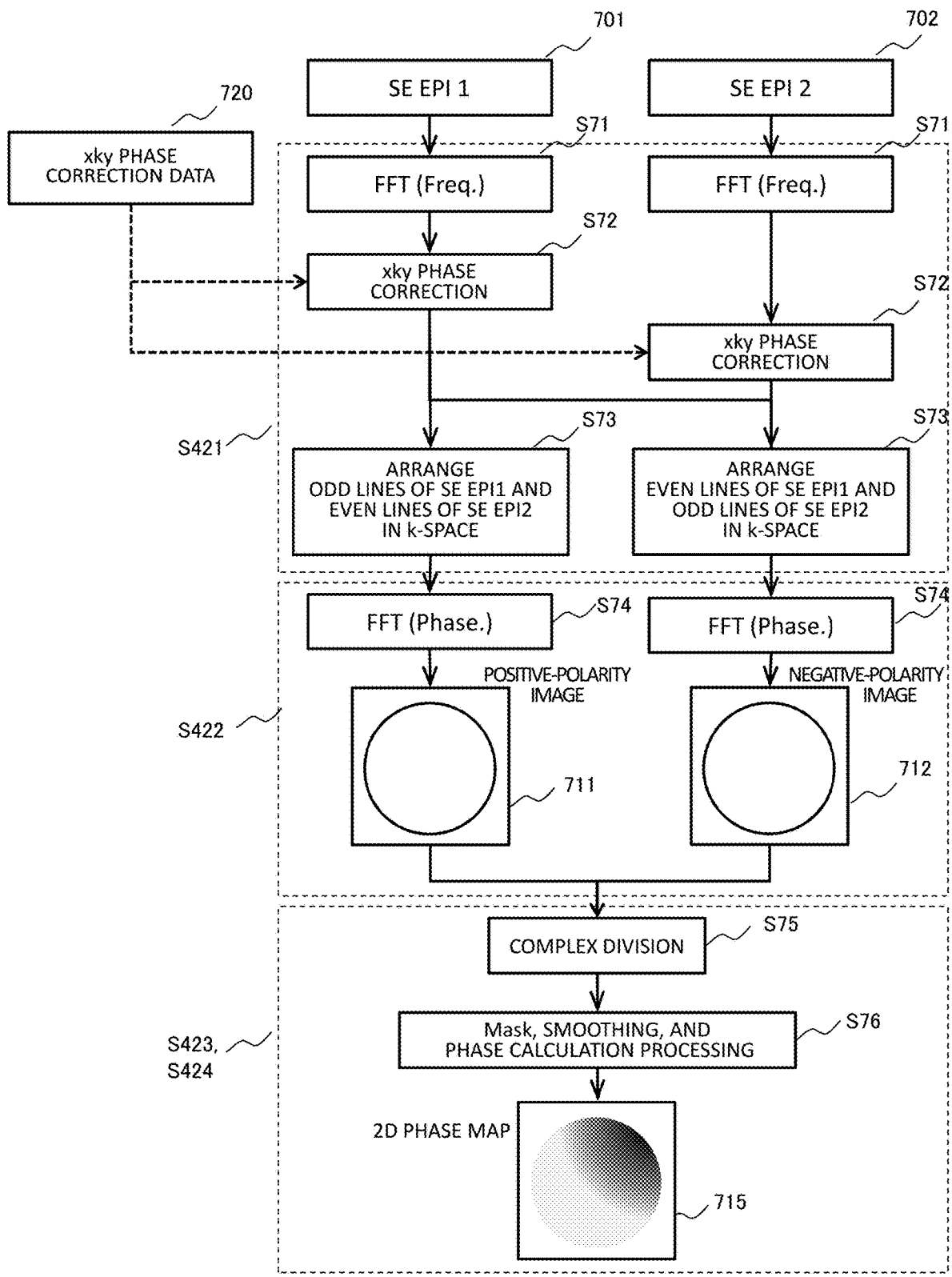
FIG. 7 is a diagram used to explain details of phase map calculation in the first embodiment.

A specific example of step S42 is further described with reference to FIG. 7.

First, in the measurement step S41 (S411), each of b0 data (+) 701 and b0 data (−) 702, obtained by imaging with b-value=0 and with the readout gradient magnetic field polarity reversed, is subjected to Fourier-transform in the readout direction, to obtained xky-space data (S71). Then, xky correction is applied to these xky-space data (S72). The xky correction is, as mentioned above, processing for correcting the gradient of a phase profile appearing in the readout direction of xky-space (low-order correction), and can be performed with use of previously-acquired data for xky correction 720. Furthermore, xky correction only needs to be applied as needed, for example, in a case where there is a large error between echoes, and can also be omitted.

Next, with respect to data obtained by xky correction, odd lines and even lines (S73 and S422 in FIG. 6) are rearranged. Specifically, the phase map calculation unit 25 calculates one of xky-space data with use of odd lines of xky-space data of b0 data (+) and even lines of xky-space data of b0 data (−), and generates another of xky-space data with use of even lines of xky-space data of b0 data (+) and odd lines of xky-space data of b0 data (−). In the case of omitting xky correction, odd/even lines of b0 data (+) 701 and odd/even lines of b0 data (−) 702, which are kxky-space data, are rearranged.

After that, the xky-space data is subjected to Fourier-transform in the phase encode direction, or, in the case of omitting xky correction, k-space data is subjected to two-dimensionally Fourier-transform (S74), and thus positive-polarity and negative-polarity images 711 and 712 with low-order phase errors corrected are obtained. Next, the positive-polarity image 711 and the negative-polarity image 712 are subjected to complex division (S75) to obtain a phase map representing positive-polarity and negative-polarity errors. Since the phase map is calculated from images which do not contain low-order phase errors, it represents high-order phase errors.

Since, in the phase map obtained by complex division, phase information other than that in a test subject region is unnecessary, mask processing for removing information other than that in the test subject region (S76) is performed. The mask processing can include calculating a mask by a general method of, for example, calculating threshold values from, for example, a positive-polarity absolute-value image by, for example, a discriminatory analysis method and binarizing the threshold values, and multiplying the phase map obtained by complex division by the calculated mask. Moreover, for the purpose of reducing the influence of noises or local errors (for example, a failure in mask), smoothing can be performed on the phases. While a general method of, for example, applying a median or Hamming filter can be employed for smoothing, it is desirable to use an adaptive low-pass filter or polynomial approximation to prevent or reduce a rapid phase change in a mask boundary. With these processing operations, a 2D phase map 715 representing errors (high-order errors) between even and odd echoes is calculated.

[Correction Step S43]

In the present step, the correction unit 23 corrects data for image acquired by DWI imaging with use of the 2D phase map 715 calculated by the phase map calculation unit 25 in the above-mentioned step S42.

The correction step S43 includes, as illustrated in FIG. 6(C), step S431 which performs low-order phase correction on the DWI imaging data acquired in S412 to S414 (FIG. 6(A)) of the measurement step, step S432 which rearranges even lines and odd lines, step S433 which acquires an odd-line image and an even-line image by Fourier transform, step S434 which performs 2D phase correction on the odd-line image and the even-line image with use of the phase map 715 obtained in the above-mentioned step S42, step S435 which performs complex addition of the odd-line image and the even-line image obtained by phase correction, and step S436 which obtains absolute values and thus acquires an image obtained by correction.

Figure 8:
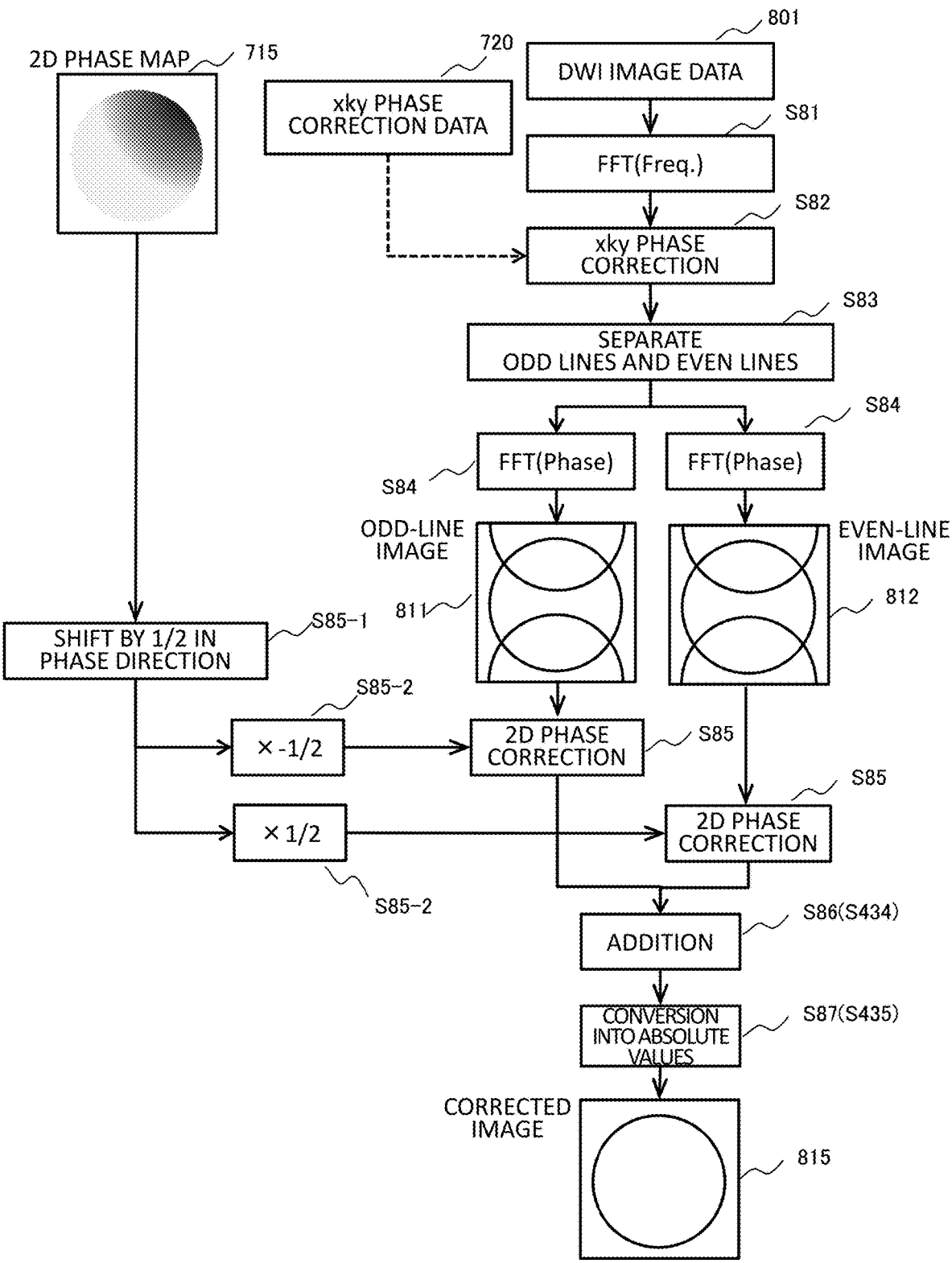
FIG. 8 is a diagram used to explain details of two-dimensional phase correction (Nyquist ghost correction) in the first embodiment.

A specific example of the present step is further described with reference to FIG. 8.

First, the correction unit 23 performs low-order phase correction on data for DWI image 801 acquired in DWI imaging S412 to S414 (S431). Specifically, the data for DWI image 801 is subjected to Fourier-transform in the readout direction, to obtain xky-space data (S81). Then, xky phase correction is applied to the xky-space data with use of xky phase correction data 720 (S82). The xky phase correction data 720 can be data acquired by preliminary imaging as with the data used in xky phase correction in the phase map calculation step S42. Even in this case, if an error between each echo is small, xky phase correction is unnecessary.

Next, the correction unit 23 separates odd lines and even lines in the data for DWI image 801 (S83). In separating odd lines, even lines are zero filled, and, in separating even lines, odd lines are zero filled. The respective of data is subjected to Fourier transform in the phase encode direction, and thus an odd-number image 811 and an even-line image 812 (S84) are generated. In the images 811 and 812, which have been generated with odd lines and even lines separated, while low-order errors between odd lines and even lines have been reduced, high-order errors in the readout direction and errors in the phase encode direction still remain.

With respect to the odd-number image 811 and the even-line image 812 in which such high-order errors remain, the correction unit 23 corrects two-dimensional phase errors with use of the 2D phase map 715 calculated in step S42 (S85). In the two-dimensional phase correction using the 2D phase map 715, as illustrated in FIG. 8, after shifting the 2D phase map 715 by one-half (½) thereof in the phase encode direction, the two-dimensional phase correction is applied to the odd-number image 811 and the even-line image 812. Here, it is necessary to invert computations in phase correction according to on which of the data 701 and the data 702 obtained by reversing readout in FIG. 7 the 2D phase map 715 is based. For example, in a case where the 2D phase map 715 is a map representing a phase difference that is based on odd lines, division processing for subtracting phase correction values of the phase map is performed with respect to the odd-line image 811, and multiplication processing for adding phase correction values of the phase map is performed with respect to the even-line image 812.

The correction unit 23 performs complex addition on the odd-line image 811 and the even-line image 812 obtained by two-dimensional phase correction (S86), and performs conversion into absolute values (S87), thus obtaining an image 815 with errors including high-order phase errors phase-corrected.

The above-described processing in the correction step S43 is applied to all of the pieces of image data obtained in S412 to S413 of the measurement step. Moreover, in a case where the number of times of addition is two or more, it is desirable to add an absolute-value image after applying two-dimensional phase correction processing for each image obtained by imaging.

[Diffusion Image Generation Step S44]

The image generation unit 21 calculates a diffusion image, such as a diffusion trace image or an ADC map, with use of corrected images obtained in every application direction of MPG pulses and images with b-value=0 used for phase map calculation. While the method of generating such a diffusion image is the same as a conventional method and the detailed description thereof is omitted, in the case of a diffusion trace image, for example, corrected images in the AP direction, RL direction, and HF direction are combined to generate an image representing the intensity of diffusion. Moreover, in the case of an ADC map, apparent diffusion coefficients (ADCs) are calculated for the respective pixels from gradients of signal values (logarithms) relative to b-values with use of images with b-value=0, to obtain an image in which values of ADCs are set as pixel values, i.e., an ADC map.

Here, as for an image with b-value=0 by, a pair of pieces of data for image (701 and 702 in FIG. 7) used for phase map calculation is used and, after applying xky phase correction as with other data for DWI image, directly complex addition of the pair of pieces of data for image is performed. Alternatively, the image generation unit 21 can generate an image with b-value=0 by adding together absolute value images of the positive-polarity image 711 and the negative-polarity image 712 generated during phase map calculation.

As described above, according to the present embodiment, since a phase map for two-dimensional phase correction is calculated with data for image whose low-order phase errors are corrected, it is possible to perform high-order and high-accuracy phase correction. Moreover, according to the present embodiment, since a 2D phase map used for performing two-dimensional phase correction is calculated with use of data for image with b-value=0 acquired for diffusion image generation in DWI imaging, it is possible to obtain a DWI image where Nyquist ghosts are reduced, without the need for additional reference imaging.

Modification Example of First Embodiment

While, in the first embodiment, a case where a phase map is calculated with use of data for image with b-value being zero in DWI imaging and images with other b-values are corrected with use of the phase map has been described, even images with b-value being zero, from which a 2D phase map has been calculated, can be corrected with use of the same 2D phase map (referred to as "self-correction"). In this case, images with b-value=0 can be corrected in the same flow (procedure illustrated in FIG. 8) as that used for images with other b-values, or can be corrected with use of images (images 711 and 712 illustrated in FIG. 7) acquired during phase map calculation.

Usually, in a case where an image contains local errors, slight shading or distortion occurs due to complex addition. Accordingly, in the case of performing complex addition of a pair of images with b-value=0 to be used for generation of a diffusion image, for example, shading may occur. However, as in the present modification example, since errors are reduced by applying two-dimensional phase correction to images themselves from which a phase map for correction has been calculated, it is possible to obtain an image with not only Nyquist ghosts but also local shading or distortion reduced.

Figure 9:
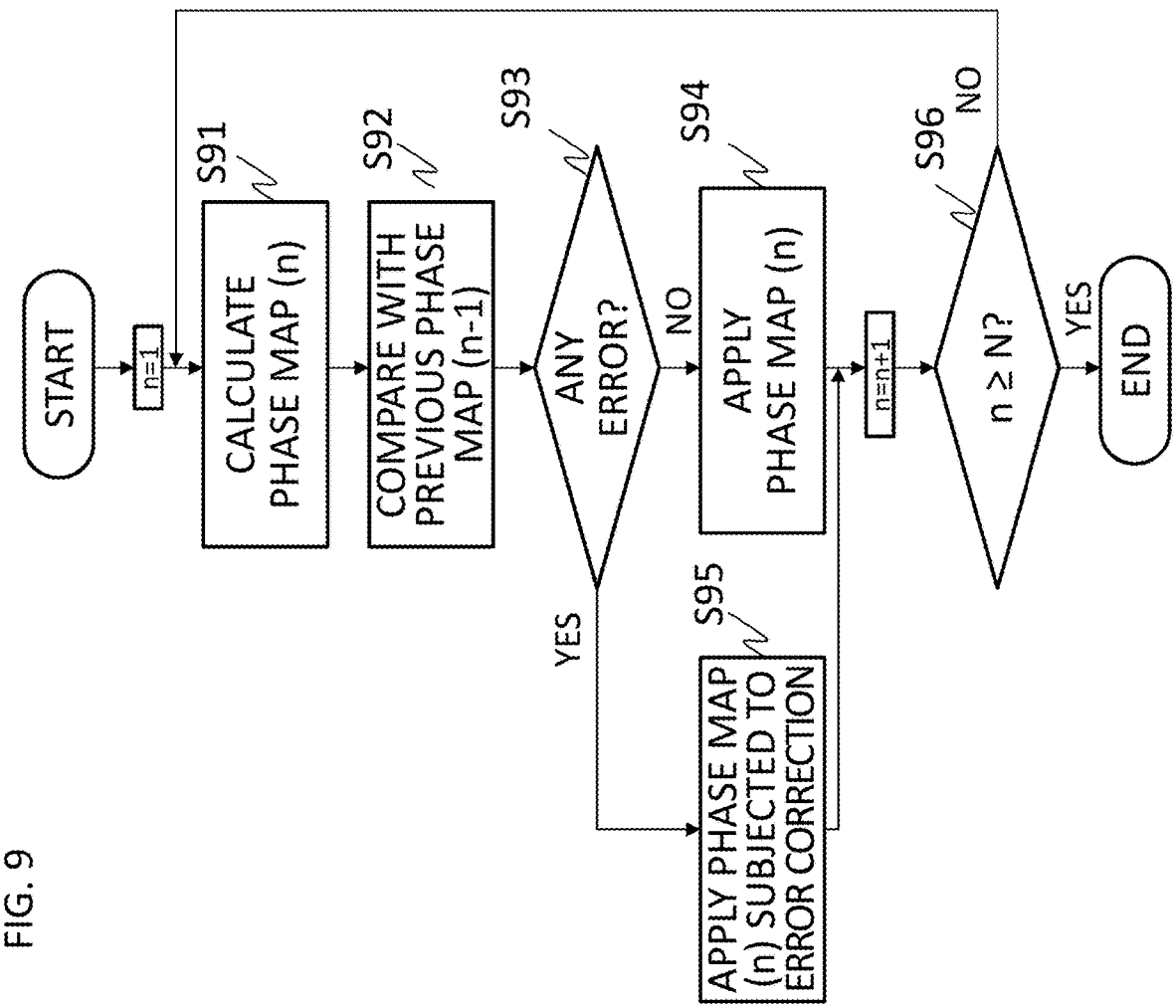
FIG. 9 is a diagram illustrating a phase map adjustment procedure in a modification example of the first embodiment.

Additionally, in the case of repeating imaging with no MPG pulses applied (imaging with b-value=0) for the number of times of addition being two or more, a phase map can be calculated for every imaging to be used for self-correction. Moreover, it is possible to identify an error portion (local portion) occurring in an unexpected fashion by comparing phase maps calculated for every imaging. In that case, it is possible to prevent image deterioration caused by phase correction, by replacing the error portion with a normal map. An example of a procedure (S91 to S96) in this case is illustrated in FIG. 9.

The determination as to whether the calculated phase map is a normal map (S93) can be performed by a method in a second embodiment described below (detection of an abnormal portion), or can be performed by use of methods other than that method. Moreover, in a case where there is no normal map to be used for replacement, an adjusted phase map obtained by adjusting a correction amount by the method in the second embodiment can be used.

Second Embodiment

The present embodiment is characterized by detecting an abnormal portion of a phase map acquired by the phase map calculation unit in the first embodiment and calculating an adjusted phase map with the abnormal portion corrected.

If Nyquist ghosts of an image used for phase map calculation (in the first embodiment, an image with b-value=0, hereinafter referred to as an "image for map") have been sufficiently reduced, a calculated phase map appropriately represents errors between even and odd echoes. On the other hand, under a condition in which errors caused by hardware control occur to a large degree, for example, when in-plane oblique scan is performed during imaging, there is a case where errors between even and odd echoes cannot be completely corrected and artifacts such as Nyquist ghosts remain in the image for map. The phase map calculated in this state does not appropriately represent errors between even and odd echoes, and, when being applied to a DWI image, causes image deterioration such as signal loss. Therefore, the present embodiment is configured to detect an abnormal portion from a phase map and adjust a phase correction amount, thus reducing image deterioration such as signal loss of a DWI image.

Figure 10:
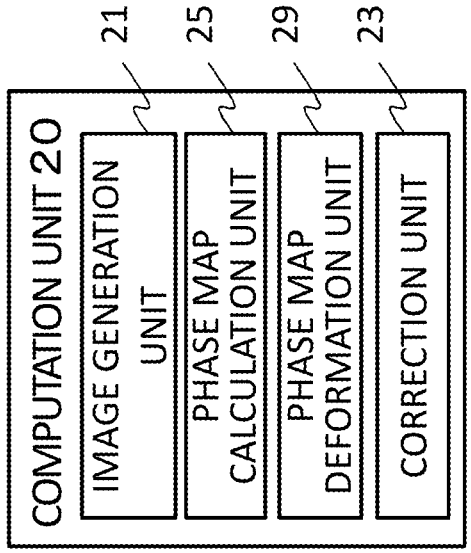
FIG. 10 is a functional block diagram of a computation unit in a second embodiment.

A configuration of the computation unit 20 in the present embodiment is illustrated in FIG. 10. In FIG. 10, the same elements as those illustrated in FIG. 1 are denoted by the respective same reference characters and any duplicate description thereof is omitted. As illustrated in FIG. 10, the computation unit 20 in the present embodiment includes a phase map adjustment unit 27 which corrects any abnormal portion of a 2D phase map calculated by the phase map calculation unit 25. Procedures of calculation of a 2D phase map and phase correction using an adjusted phase map in the computation unit 20 are similar to those in the first embodiment, and, therefore, the present embodiment is described as follows with a focus on differences from the first embodiment.

Figure 11:
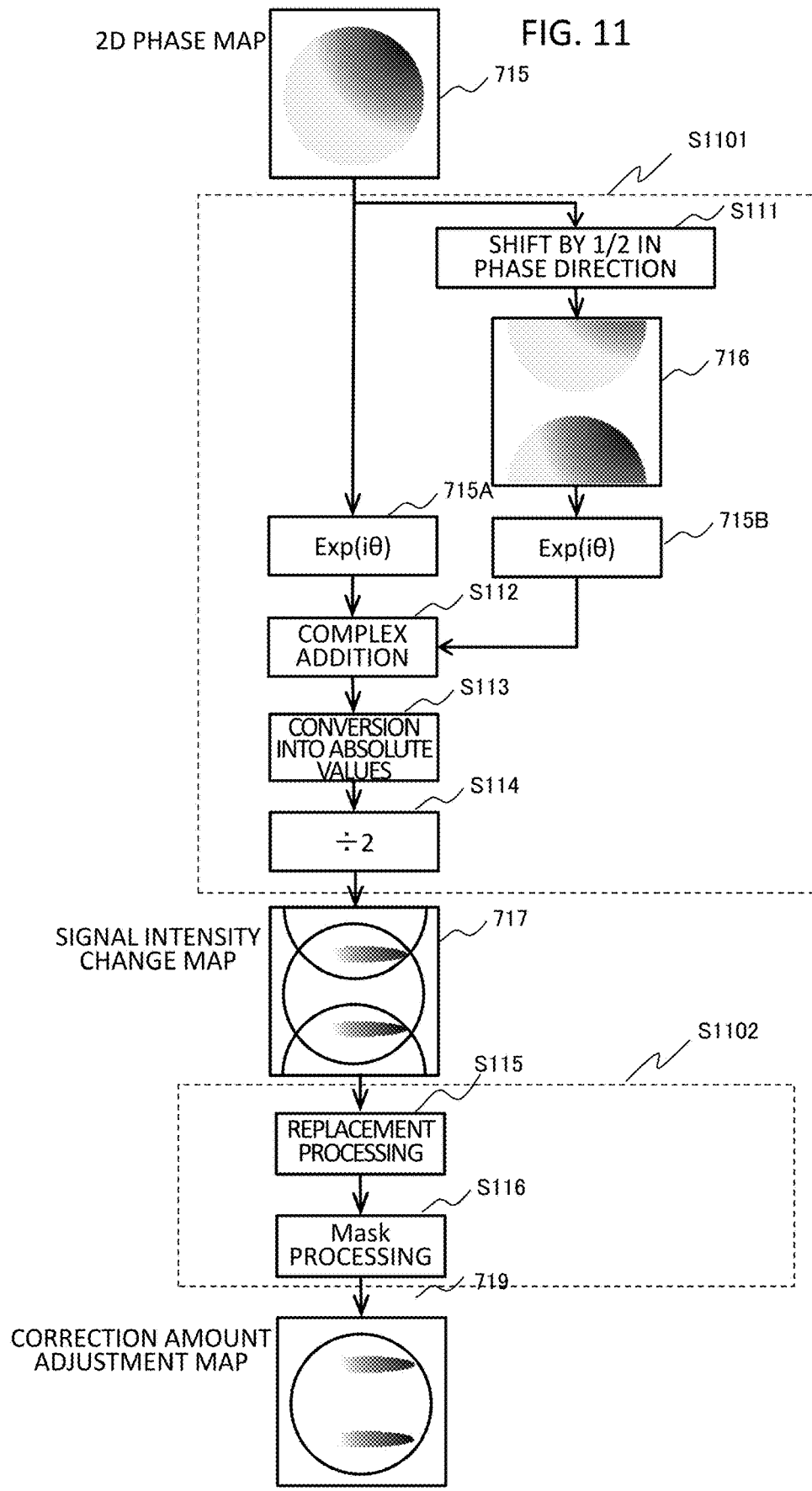
FIG. 11 is a diagram illustrating a phase map adjustment procedure in the second embodiment.

FIG. 11 illustrates a processing procedure which the phase map adjustment unit 27 in the present embodiment performs. As indicated by surrounding dotted-line squares illustrated in FIG. 11, the phase map adjustment unit 27 performs processing S1101 for calculating a map representing signal intensity changes (a signal intensity change map) with use of the calculated 2D phase map (715 in FIG. 7) and processing S1102 for determining a correction amount adjustment value based on the signal intensity changes in the signal intensity change map and calculating a correction amount adjustment map.

In the following description, each processing operation is specifically described with reference to FIG. 11.

In the signal intensity change map calculation processing S1101, the phase map adjustment unit 27 calculates complex data 715A and 715B ($Exp(i\theta)$), the absolute value of each of which is 1, from a phase map 715 calculated by the phase map calculation unit 25 and a phase map 716 obtained by shifting the phase map 715 by one-half (½) thereof in the phase encode direction (S111). Complex addition of these pieces of complex data (S112) is performed, and a complex addition result is converted into an absolute value and divides the absolute value by 2 (S113 and S114), to obtain a signal intensity change map 717. This map 717 represents the amount of change in signal value occurring when two-dimensional phase correction processing is applied. In the signal intensity change map 717 illustrated in FIG. 11, a circle at the center thereof represents a test subject portion, and a semicircle of the upper limit represents a portion of ghosts.

Usually, since the ghost amount (the amount of change in signal value occurring due to ghosts) is about half of the signal value of an image, in portions where a test object and ghosts overlap each other (portions where a central circle and upper and lower semicircles in the map 717 overlap each other), it is rare that the signal value becomes half or less due to two-dimensional phase correction processing. Accordingly, it is expected that numerical values in the signal intensity change map 717 (values of the proportion of a changed signal intensity to an original signal intensity, i.e., values of the rate of change of signal intensity) are distributed within the range of 0.5 to 1.0. Thus, a portion in which an expected numerical value is out of the above-mentioned range has an extremely high probability of being abnormal in intensity change. For example, while a portion in which the rate of change is 0.1 causes a signal value to disappear, a condition in which a signal value disappears in a portion which a subject overlaps is an obvious error. With respect to such an error portion, a correct correction cannot be expected.

Figure 12:
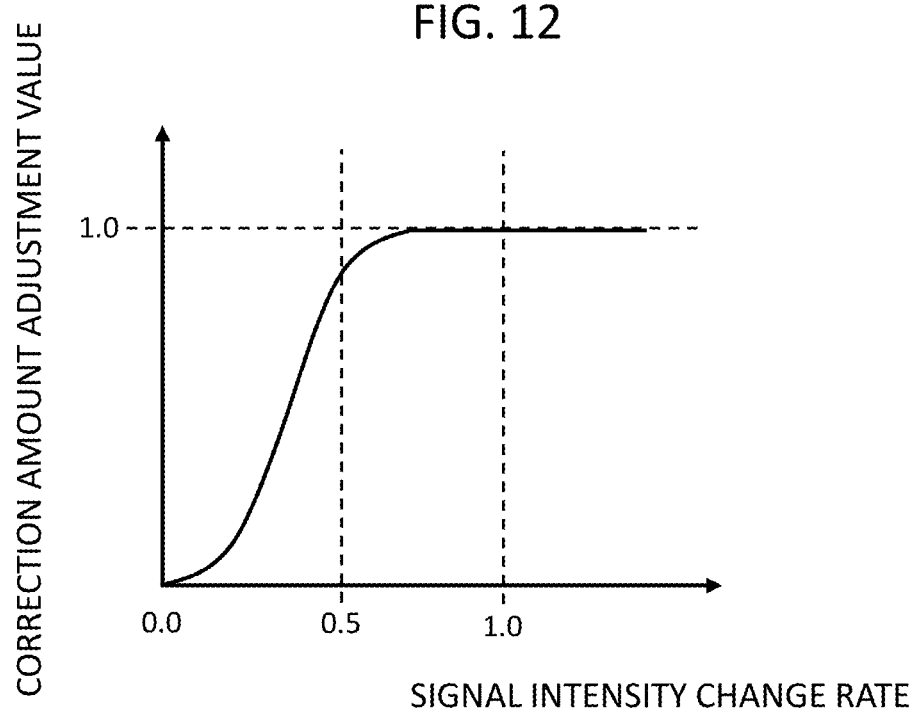
FIG. 12 is a diagram illustrating an example of an LUT for use in phase map adjustment in the second embodiment.

Therefore, in the processing S1102 for calculating a correction amount adjustment map, with regard to a portion (abnormal portion) in which numerical values in the signal intensity change map 717 are out of a predetermined range (for example, 0.5 to 1.0, or), the phase map adjustment unit 27 determines an adjustment value, which is used to adjust a correction value for a corresponding portion on the 2D phase map 715, based on a previously-set relationship between signal values and adjustment values. An example of a graph representing a relationship between the signal intensity change rate and the correction amount adjustment value is illustrated in FIG. 12. This graph is an example of a look-up table (LUT) generated in consideration of the probability of being statistically an error based on such knowledge that, as the numerical value is further away from the predetermined range, the probability of being an error increases, and is a graph obtained by plotting each adjustment value to be multiplied by a correction value in the phase map with respect to the signal intensity change rate.

Next, the phase map adjustment unit 27 replaces the signal intensity change map 717 by correction amount adjustment values (S115), extracts a test subject region by mask processing (S116), and obtains a correction amount adjustment map 719. If the intensity change rate at the same position in the signal intensity change map is 0.5, then the corresponding correction amount adjustment amount is about 0.8 in reference to the LUT. The correction amount adjustment map 719 is used for two-dimensional phase correction of a DWI image together with the 2D phase map 715.

Figure 13:
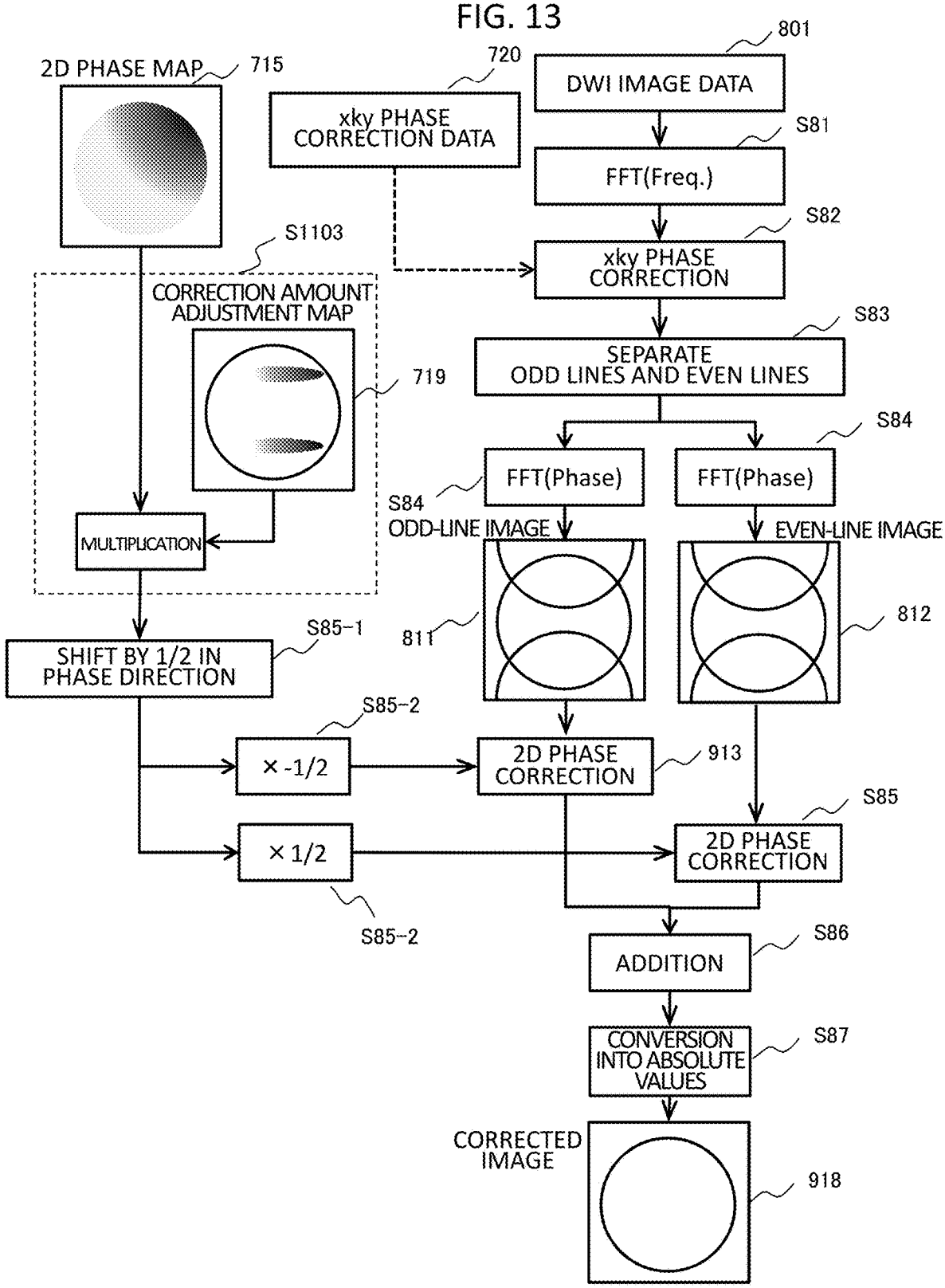
FIG. 13 is a diagram used to explain details of two-dimensional phase correction in the second embodiment.

While the method for two-dimensional phase correction of a DWI image in the present embodiment is almost the same as that in the first embodiment, as indicated by a surrounding dotted-line square illustrated in FIG. 13, before two-dimensional phase correction using the 2D phase map 715, processing for adjusting the correction amount in the 2D phase map 715 with use of the above-mentioned correction amount adjustment map 719 is added. Thus, the correction unit 23 in the present embodiment performs two-dimensional phase correction on DWI image data (an odd-line image and an even-line image) obtained by xky correction and low-order phase correction with use of a map (an adjusted phase map) obtained by multiplying the 2D phase map 715 by the correction amount adjustment map 719 (S1103), performs complex addition, and performs conversion into absolute values, thus obtaining a corrected image.

According to the present embodiment, detecting an error portion (abnormal portion) in a 2D phase map calculated by the phase map calculation unit 25 and then performing two-dimensional phase correction with values of the error portion replaced enables reducing a signal loss caused by an error occurring during phase map calculation and performing higher-accuracy phase correction. With this, even in a case where an artifact occurs in an image with b-value=0 for use in diagnosis, a DWI image with image deterioration such as signal loss reduced is obtained.

Furthermore, while, in the above description, as the function of the phase map adjustment unit 27, performing processing from detection of an abnormal portion to calculation of a correction amount adjustment value map has been described, naturally, up to processing for calculating an adjusted phase map by multiplying the phase map 715 by the correction amount adjustment value map can be set as the function of the phase map adjustment unit 27. In this case, processing to be performed by the correction unit 23 illustrated in FIG. 13 becomes similar to that illustrated in FIG. 8 except that the phase map 715 is replaced by the adjusted phase map.

Moreover, even in the present embodiment, a modification example similar to that of the first embodiment can be employed.

Third Embodiment

The phase map and the correction amount adjustment map calculated in the first embodiment and the second embodiment vary depending on an imaging condition and a test subject, but the characteristics thereof themselves have roughly the same tendency. The present embodiment is characterized by, with use of that effect (tendency), previously acquiring and storing a phase map by use of, for example, a phantom and using such information as a reference. Furthermore, this reference is different from a conventional reference image which is acquired during imaging, and is an image which is acquired in a situation different from actual imaging, such as during installation of the MRI device.

Figure 14:
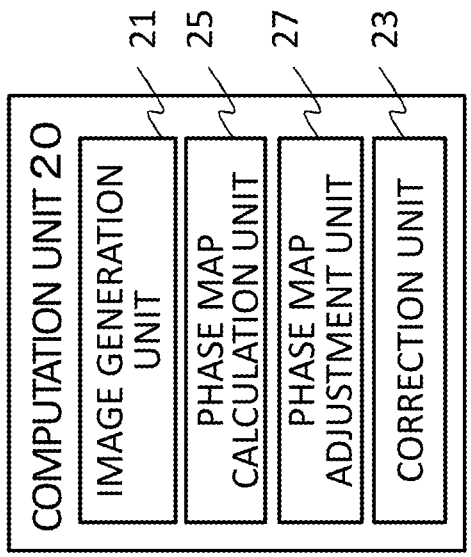
FIG. 14 is a functional block diagram of a computation unit in a third embodiment.

A configuration of the computation unit 20 in the present embodiment is illustrated in FIG. 14. In FIG. 14, the same elements as those illustrated in FIG. 1 are denoted by the respective same reference characters and any duplicate description thereof is omitted. As illustrated in FIG. 14, the computation unit 20 in the present embodiment includes a phase map deformation unit 29 which compares a phase map calculated by the phase map calculation unit 25 (referred to as a "main-imaging phase map") with a phase map previously stored in the storage unit 50 (referred to as a "during-installation phase map"), deforms the during-installation phase map in conformity with the main-imaging phase map, and thus calculates a deformed phase map.

With regard to the during-installation phase map, for example, EPI imaging is performed with a plurality of imaging conditions using a phantom, for example, during installation of the MRI device, and a phase map for two-dimensional phase correction is calculated with use of the obtained images, for example, by a method similar to the method described in the first embodiment or a conventional method of acquiring data with the FOV doubled, and the calculated phase map is stored in the storage unit 50.

Figure 15:
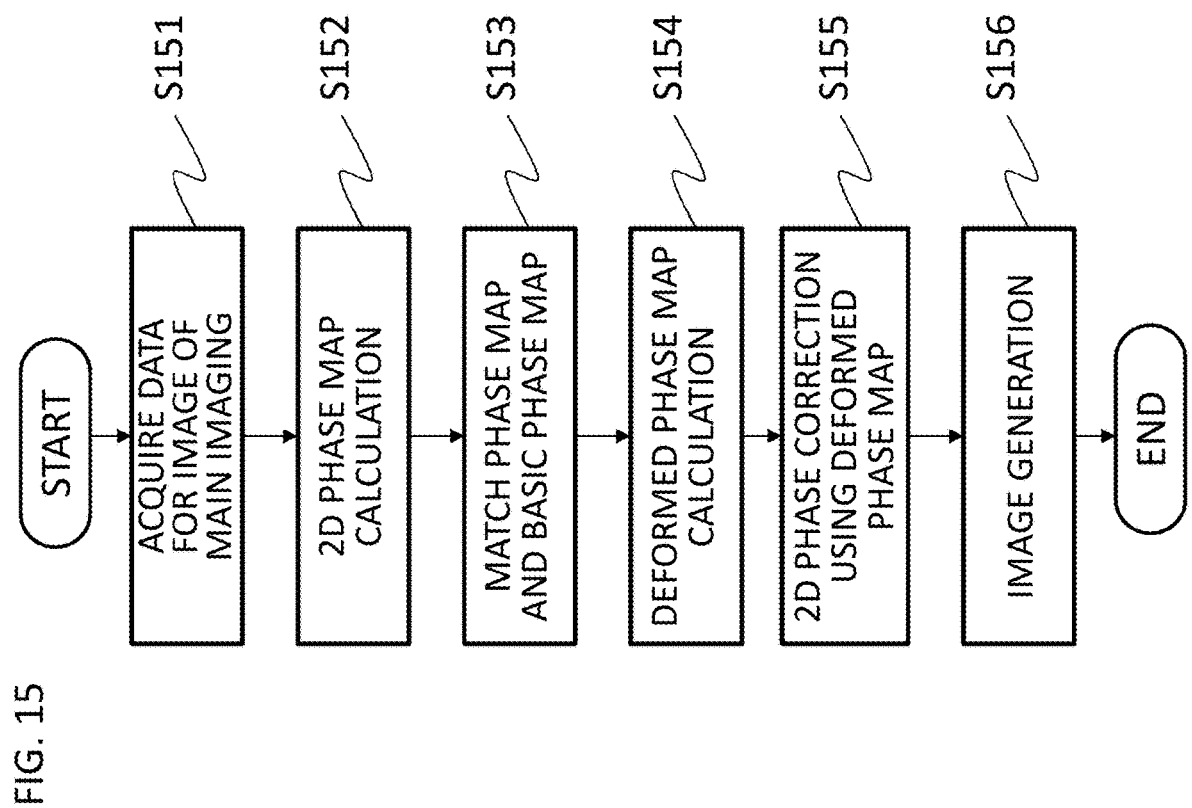
FIG. 15 is a diagram illustrating a processing procedure in the third embodiment.

In the following description, an operation of the computation unit 20 in the present embodiment is described with reference to a flow illustrated in FIG. 15. Processing which is performed by the computation unit 20 is similar to that in the first embodiment except for the phase map deformation unit 29 calculating a deformed phase map (S153 and S154) and the correction unit 23 using the deformed phase map in two-dimensional phase correction (S155). The following description is made with a focus on differences from the first embodiment.

The phase map calculation unit 25 calculates a 2D phase map (main-imaging phase map) from data for image acquired by main imaging by a method similar to that in the first embodiment (S151 and S152). For example, suppose that a 2D phase map 1601 such as that illustrated in FIG. 16(*a*) has been obtained. While, in this figure, a phase map is expressed by a line profile in the readout direction, the 2D phase map is a two-dimensional map also including phases in the phase encode direction. In this example, a local error is occurring at a portion 1602 surrounded by a dotted line.

The phase map deformation unit 29 calculates a primary gradient and a phase change amount in each of the readout direction and the phase encode direction by, for example, polynomial approximation from the 2D phase map 1601 (S153-1). On the other hand, the phase map deformation unit 29 reads out, from the storage unit 50, a phase map 1603 (FIG. 16 (*b*)) acquired with the same imaging condition as that of main imaging out of phase maps (during-installation phase maps) calculated from data for image acquired by imaging with, for example, a phantom, and deforms the during-installation phase map 1603 with use of the primary gradient and the phase change amount obtained in step S153-1 (S153-2). Deformation can be performed by, for example, adding the primary gradient in each of the readout direction and the phase encode direction to a phase of during-installation data or multiplying the phase of during-installation data by a fixed value. Thus, a deformed phase map 1605 (FIG. 16(*c*)) (S153 and S154) is obtained.

The correction unit 23 performs two-dimensional phase correction of an image obtained by main imaging (regardless of including an image used for calculation of the phase map 1601 or not) with use of the deformed phase map 1605 obtained in the above-described way. This processing is the same as the correction processing in the first embodiment illustrated in FIG. 8. Since the deformed phase map 1605 does not include a local error (1602), which comes to be mixed therein during main imaging, using the deformed phase map 1605 for two-dimensional phase correction causes image deterioration of a finally obtained image to be reduced.

Figure 16:
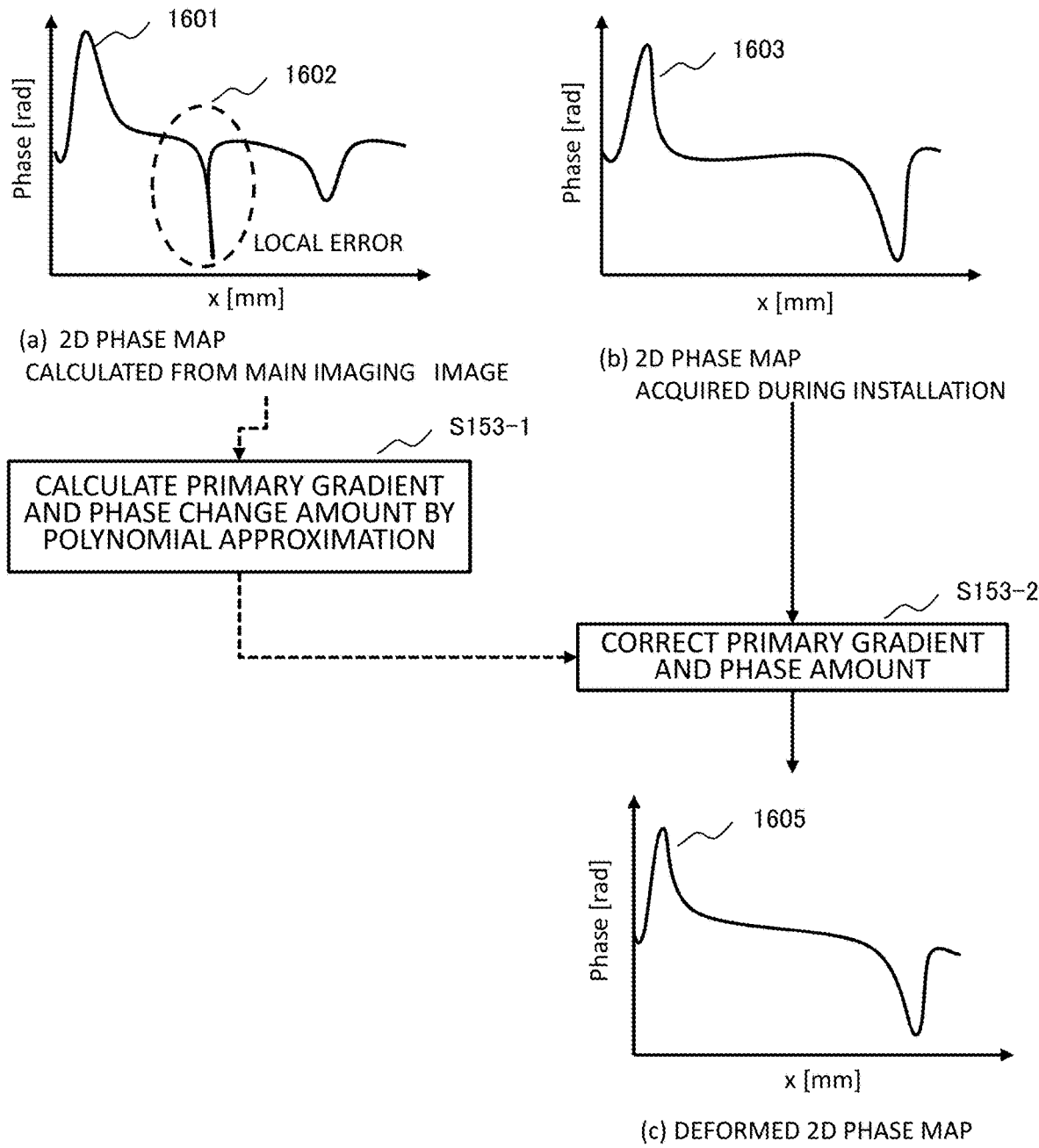
FIG. 16 is a diagram used to explain a procedure of phase map deformation performed in the third embodiment.

In the processing illustrated in FIG. 16, a gradient and a phase change amount are obtained from the 2D phase map 1601 obtained by main imaging, and the during-installation phase map 1603 is deformed in conformity with these. However, such processing can be configured such that the during-installation phase map 1603 is compared with the main-imaging phase map 1601 while successively deforming a primary gradient and a phase change amount in the during-installation phase map 1603 and a phase change amount obtained when an error between the two maps become minimum is set as an optimum change amount.

According to the present embodiment, deforming a during-installation phase map previously acquired for each imaging condition in conformity with a 2D phase map obtained by main imaging and then applying the during-installation phase map to two-dimensional phase correction enables increasing the accuracy of correction. Moreover, according to the present embodiment, since comparing deformed during-installation data with a main-imaging phase map enables finding an abnormal portion and its degree in a main-imaging phase map, as with the second embodiment, it is also possible to calculate and apply a correction amount adjustment map, so that, with this, image deterioration caused by two-dimensional phase correction can be further reduced.

Fourth Embodiment

Figure 17:
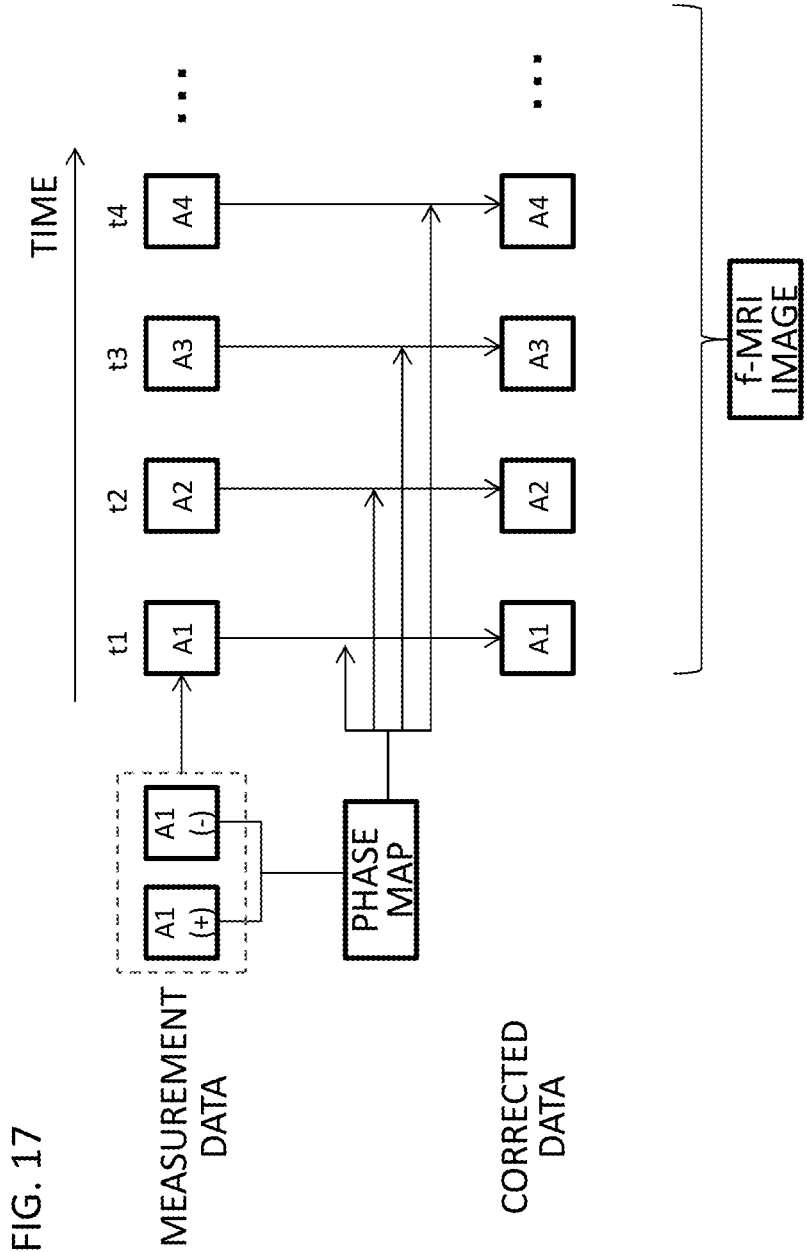
FIG. 17 is a diagram illustrating processing in a fourth embodiment.

While, in the first embodiment, the case of performing DWI imaging has been described, the present invention is characterized by calculating a phase map for use in Nyquist ghost correction from data for image obtained by imaging of a test subject, and is able to be applied to not only DWI imaging but also all of the types of imaging as long as imaging which causes an EPI sequence to repeatedly operate, such as functional imaging (f-MRI) which acquires time-series images of a test subject. In that case, as illustrated in FIG. 17, a 2D phase map can be calculated from, for example, an image A1 first acquired out of time-series images A1, A2, . . . , and subsequent pieces of image data can be corrected with the calculated 2D phase map. Moreover, as described in the modification example (FIG. 9) of the first embodiment, calculating a 2D phase map for each or every plurality of operations of imaging and comparing the calculated 2D phase maps can be used to perform detection of an error in a 2D phase map or replacement by a normal phase map.

While various embodiments and modification examples of the MRI device and Nyquist correction in the present invention have been described above, omitting a part of the processing operations described in these embodiments or adding known processing operations is also included in the present invention.

REFERENCE SIGNS LIST

10 . . . measurement unit, 14 . . . measurement control unit, 20 . . . computation unit, 21 . . . image generation unit, 25 . . . phase map calculation unit, 23 . . . correction unit, 27 . . . phase map adjustment unit, 29 . . . phase map deformation unit, 30 . . . control unit, 40 . . . user interface unit, and 50 . . . storage unit.

The invention claimed is:

1. A magnetic resonance imaging device comprising:
a measurement unit that acquires a plurality of pieces of data for image with use of an EPI method;
a phase map calculation unit that calculates
a phase map using at least one of the plurality of data for image measured by the measurement unit; and
a correction unit that corrects a Nyquist ghost included in the data for image with use of the phase map calculated by the phase map calculation unit,
wherein the phase map calculation unit performs low-order phase correction with use of a pair of k-space data different in only polarity of readout gradient magnetic field of the data for image used for phase map calculation, and calculates a two-dimensional phase map in which a remaining two-dimensional phase error is set as a correction amount, and wherein, after performing low-order phase correction on data for image targeted for correction, the correction unit corrects the Nyquist ghost with use of the two-dimensional phase map.

2. The magnetic resonance imaging device according to claim 1, wherein the phase map calculation unit calculates the two-dimensional phase map using a pair of image data obtained by respectively reconstructing k-space data obtained by combining odd lines of one of the pair of k-space data different in only polarity of readout gradient magnetic field and even lines of the other of the pair of k-space data and k-space data obtained by combining even lines of one of the pair of k-space data and odd lines of the other of the pair of k-space data.

3. The magnetic resonance imaging device according to claim 1, wherein the correction unit corrects data for image used for calculation of the two-dimensional phase map as the data for image targeted for correction.

4. The magnetic resonance imaging device according to claim 1, further comprising a phase map adjustment unit that detects an abnormal portion included in the two-dimensional phase map and adjusts a correction value for the abnormal portion,
wherein the correction unit performs correction of the data for image with use of the adjusted two-dimensional phase map.

5. The magnetic resonance imaging device according to claim 4, wherein the phase map adjustment unit generates an intensity change map representing a change in signal intensity with use of the two-dimensional phase map not yet adjusted, and determines a correction value adjustment amount for the abnormal portion based on a relationship between a previously set signal intensity change and a correction value adjustment amount.

6. The magnetic resonance imaging device according to claim 1, wherein the plurality of data for image which the measurement unit measures is data for DWI image different in b-value of MPG pulses, and
wherein the phase map calculation unit calculates the two-dimensional phase map with use of data for image with b-value being zero.

7. The magnetic resonance imaging device according to claim 1, wherein the measurement unit performs measurement of a set of data for image different in polarity of readout gradient magnetic field a plurality of times, and
wherein the phase map calculation unit calculates the two-dimensional phase map with use of the set of data for image for each measurement of the set of data for image.

8. The magnetic resonance imaging device according to claim 1, wherein the plurality of data for image which the measurement unit measures is time-series data for image acquired in a temporally successive manner, and
wherein the phase map calculation unit calculates the two-dimensional phase map with use of data for image first acquired out of the time-series data for image.

9. The magnetic resonance imaging device according to claim 1, further comprising:
a storage unit that stores two-dimensional phase maps representing phase errors occurring during measurement performed by an EPI method previously acquired with a plurality of different imaging conditions; and
a phase map deformation unit that deforms at least one of the two-dimensional phase maps stored in the storage unit with use of phase information about the two-dimensional phase map calculated by the phase map calculation unit,
wherein the correction unit performs correction of the data for image with use of a deformed phase map calculated by the phase map deformation unit.

10. A Nyquist ghost correction method for correcting Nyquist ghosts in a plurality of images obtained by imaging using an EPI method, the Nyquist ghost correction method comprising:
acquiring a pair of k-space data different in polarity of readout gradient magnetic field with respect to at least one image out of the plurality of images;
generating a pair of image data subjected to low-order phase correction from k-space data obtained by performing rearrangement of odd lines and even lines of the pair of k-space data and combining odd lines of one of the pair of k-space data and even lines of the other of the pair of k-space data and k-space data obtained by combining even lines of one of the pair of k-space data and odd lines of the other of the pair of k-space data;
calculating a two-dimensional phase map in which phase differences calculated by performing complex division of the pair of image data are set as pixel values; and
correcting the plurality of images with use of the two-dimensional phase map.

11. The Nyquist ghost correction method according to claim 10, further comprising:
performing the low-order phase correction on each of a pair of xky-space data obtained by performing Fourier transform of each of the pair of k-space data in a readout direction; and
after rearranging odd lines and even lines in the pair of xky-space data, performing Fourier transform of the rearranged xky-space data in a phase encode direction to generate the pair of image data.

12. The Nyquist ghost correction method according to claim 10, further comprising, after performing complex division of the pair of image data, performing at least one of mask processing and smoothing on the pair of image data to calculate the two-dimensional phase map.

13. The Nyquist ghost correction method according to claim 10, further comprising:
separating odd lines and even lines from each other with respect to k-space data about an image targeted for correction to generate an odd-line image and an even-line image;
performing two-dimensional phase correction using the two-dimensional phase map with respect to the odd-line image and the even-line image; and
performing complex addition of the odd-line image and the even-line image subjected to two-dimensional phase correction to obtain a corrected image.

14. The Nyquist ghost correction method according to claim 13, wherein the two-dimensional phase correction includes shifting the two-dimensional phase map by one-half ($1/2$) thereof in a phase encode direction, dividing one of the odd-line image and the even-line image by the shifted two-dimensional phase map, and multiplying the other of the odd-line image and the even-line image by the shifted two-dimensional phase map.

15. A non-transitory computer-readable medium having a program for Nyquist ghost correction that causes a computer to perform:
a step of calculating a two-dimensional phase map with use of at least one of a plurality of data for image measured by a magnetic resonance imaging device; and
a step of correcting a Nyquist ghost included in the data for image with use of the calculated two-dimensional phase map, wherein the step of calculating a two-dimensional phase map includes a step of performing low-order phase correction with use of a pair of k-space data different in only polarity of readout gradient magnetic field of the data for image for use in phase map calculation, and calculating a phase map in which a remaining phase error is set as a correction amount, and wherein the step of correcting includes a step of, after performing low-order phase correction on data for image targeted for correction, performing two-dimensional phase correction on the data for image targeted for correction with use of the two-dimensional phase map.

\* \* \* \* \*